(12) United States Patent
Polster

(10) Patent No.: US 9,153,045 B2
(45) Date of Patent: Oct. 6, 2015

(54) AUGMENTED RECONSTRUCTION FOR COMPUTED TOMOGRAPHY

(71) Applicant: THE CLEVELAND CLINIC FOUNDATION, Cleveland, OH (US)

(72) Inventor: Joshua M. Polster, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 275 days.

(21) Appl. No.: 13/802,852

(22) Filed: Mar. 14, 2013

(65) Prior Publication Data

US 2013/0251228 A1    Sep. 26, 2013

Related U.S. Application Data

(60) Provisional application No. 61/614,097, filed on Mar. 22, 2012.

(51) Int. Cl.
*G06T 11/00* (2006.01)
*A61B 6/03* (2006.01)
*A61B 6/00* (2006.01)

(52) U.S. Cl.
CPC ............... *G06T 11/003* (2013.01); *A61B 6/032* (2013.01); *A61B 6/505* (2013.01); *A61B 6/5205* (2013.01); *G06T 11/008* (2013.01); *G06T 2211/40* (2013.01)

(58) Field of Classification Search
CPC .......................... G06T 11/008; G06T 2211/40
USPC ....................................................... 382/131
See application file for complete search history.

(56) References Cited

U.S. PATENT DOCUMENTS

| 5,839,440 | A | 11/1998 | Liou et al. |
|---|---|---|---|
| 7,123,760 | B2 | 10/2006 | Mullick et al. |
| 7,148,887 | B2 | 12/2006 | Kaufman et al. |
| 7,366,278 | B2 * | 4/2008 | Fu et al. ............................ 378/4 |
| 7,397,886 | B2 | 7/2008 | Avinash et al. |
| 7,409,079 | B2 | 8/2008 | Saptharishi et al. |
| 7,426,318 | B2 | 9/2008 | Fu et al. |
| 7,432,924 | B2 | 10/2008 | Ohishi |
| 7,558,611 | B2 | 7/2009 | Arnold et al. |
| 2005/0113679 | A1 | 5/2005 | Suryanarayanan et al. |
| 2005/0163283 | A1 | 7/2005 | Bruder et al. |
| 2005/0195189 | A1 | 9/2005 | Raman et al. |

(Continued)

FOREIGN PATENT DOCUMENTS

EP      1935344 A1    6/2008

OTHER PUBLICATIONS

P T Johnson, D G Heath, D F Bliss, B Cabral, and E K Fishman, "Three-dimensional CT: real-time interactive volume rendering." American Journal of Roentgenology 1996 167:3 , 581-583.*

(Continued)

*Primary Examiner* — Utpal Shah
(74) *Attorney, Agent, or Firm* — Tarolli, Sundheim, Covell & Tummino LLP

(57) ABSTRACT

Systems and methods are provided for computer tomography (CT) imaging. An attenuation transform component configured to map voxels in a received set of cross-sectional CT images to associated brightness values according to a piecewise transform function to produce a set of transformed images. A user interface is configured to provide the set of transformed images to a user at an associated display.

11 Claims, 5 Drawing Sheets

(56) References Cited

U.S. PATENT DOCUMENTS

| | | |
|---|---|---|
| 2007/0081712 A1 | 4/2007 | Huang et al. |
| 2008/0002873 A1 | 1/2008 | Reeves et al. |
| 2008/0130833 A1 | 6/2008 | Wang |
| 2008/0137935 A1 | 6/2008 | Spahn |
| 2008/0298656 A1 | 12/2008 | Yim et al. |
| 2009/0087060 A1* | 4/2009 | Omi et al. ............ 382/131 |
| 2010/0061610 A1* | 3/2010 | Van De Haar ......... 382/131 |
| 2010/0238171 A1* | 9/2010 | Krauss ................. 345/424 |
| 2011/0019890 A1 | 1/2011 | Oikawa |
| 2011/0075905 A1 | 3/2011 | Noshi |
| 2011/0158494 A1* | 6/2011 | Bar-Shalev et al. ..... 382/131 |

OTHER PUBLICATIONS

PCT International Search Report and Written Opinion, mailed Oct. 17, 2013, pp. 1-15.

* cited by examiner

AUGMENTED RECONSTRUCTION FOR COMPUTED TOMOGRAPHY

RELATED APPLICATION

This application claims priority from U.S. Provisional Application No. 61/614,097, filed 22 Mar. 2012, the subject matter of which is incorporated herein by reference in its entirety.

TECHNICAL FIELD

The present invention relates generally to the field of medical devices, and more particularly to reconstruction methods for computed tomography.

BACKGROUND OF THE INVENTION

Computed tomography is a medical imaging procedure that utilizes computer-processed X-rays to produce tomographic images or 'slices' of specific areas of the body. These cross-sectional images are used for diagnostic and therapeutic purposes in various medical disciplines. Digital geometry processing is used to generate a three-dimensional image of the inside of an object from a large series of two-dimensional X-ray images taken around a single axis of rotation. Computed tomography produces a volume of data that can be manipulated in order to demonstrate various bodily structures based on their ability to block the X-ray beam. Although most common in medicine, computed tomography is also used in other fields, such as nondestructive materials testing.

SUMMARY OF THE INVENTION

In accordance with an aspect of the present invention, a non-transitory computer readable medium stores executable instructions including a reconstruction element configured to generate a first set of cross-sectional computed tomography (CT) images, having a first axial resolution, from the provided CT scan data. A tissue suppression component is configured to identify voxels within the first set of cross-sectional CT images representing tissues that it is desirable to suppress according to their characteristic attenuation values. An averaging component is configured to generate a second set of cross-sectional CT images, having an axial resolution less than that of the first set of cross-sectional CT images, without utilizing the voxels identified by the tissue suppression component. A user interface is configured to provide the second set of cross-sectional CT images to a user at an associated display.

In accordance with another aspect of the present invention, a non-transitory computer readable medium stores executable instructions including an attenuation transform component configured to map voxels in a received set of cross-sectional CT images to associated brightness values according to a piecewise transform function to produce a set of transformed images. A user interface is configured to provide the set of transformed images to a user at an associated display.

In accordance with yet another aspect of the present invention, a method for is provided for CT scanning. A region of interest is scanned to provide a set of axial attenuation values. A first set of cross-sectional CT images, having a first axial resolution, are generated from the provided axial attenuation values. A second set of cross-sectional CT images, having a second axial resolution less than that of the first axial resolution, is generated as a voxel-by-voxel averaging of respective subsets of the first set of cross-sectional CT images. The voxel-by-voxel averaging only utilizes voxels having attenuation values within a predefined contiguous range of attenuation values. Voxels in the second set of cross-sectional CT images are mapped to associated brightness values according to a piecewise transform function to produce a set of transformed images. The set of transformed images are displayed to the user.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
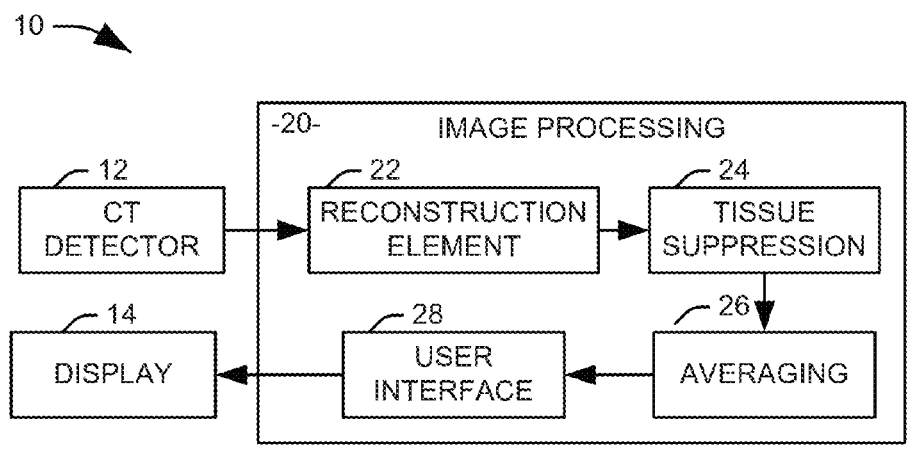
FIG. 1 illustrates a first example of a single-energy computed tomography (CT) imaging system in accordance with an aspect of the present invention.

Computed tomography (CT) scans are the standard of care for workup of cancer diagnoses in the chest abdomen and pelvis, both for detecting the primary lesion and to look for soft tissue metastatic disease. However, CT is not considered the standard of care for detecting bone metastases, even in the areas that are included on the scan since it has lower sensitivity to these lesions compared to MRI or nuclear medicine bone scintigraphy. While CT is able to image bone itself very well, it is not very good at evaluating the bone marrow, the soft tissue elements in bone where lesions start.

In general, CT images display bone as a high-attenuation, bright, white structure. It will be appreciated, however, that this is only one component of the bone, which comprises the outer mineralized portion of the bone, including the cortical bone, and a fine lattice or mesh of trabecular bone spicules that insinuate the inner portion of the bone. This trabecular network is most prominently seen in the axial skeleton, in particular vertebral bodies of the spine and in the pelvis, though also affects the ribs and the ends of long bones. If one were to look at the shaft of the long bone, one could see soft tissue components inside of the bone, usually consisting of fat attenuation, which is representative of fat marrow. The same marrow components are present within the lattice of fine trabecular spicules; however, it is insinuated between those tiny bone spicules, and thus not visible on a standard CT scan. The space between these trabecular spicules is very small, for example, on the order of one half of a millimeter.

A number of pathologic processes can occur in the soft tissue of the bone, particularly neoplastic disease. Neoplastic involvement of bone is most commonly secondary to metastatic disease from another site. When a metastasis occurs to bone marrow, it initially affects the soft tissue marrow itself without any disruption of the bone structure. In this initial phase, there is no detectable change on CT scan. MRI can detect changes by delineating a soft tissue signal nodule that displaces the normal fat marrow in that location, because the signal that returns to the MRI coil is from the soft tissue elements of the bone marrow—there is no signal return from bone itself. After further growth, there is often a stimulation of the adjacent trabecular or cortical bone, resulting in increased metabolic activity, which can be detected on a bone scan. Even at this stage, CT does not demonstrate these lesions as attenuation changes in bone. Finally, as these lesions grow, they either destroy bone, resulting in an osteolytic lesion, or stimulate bone proliferation, as is seen with osteoblastic lesions. At this point, because there are changes in the mineralized bone components themselves, CT can detect the lesions. However, in these early stages of metastatic bone disease, CT does not currently demonstrate changes.

There are significant clinical consequences to the lack of detection of these lesions at an early stage. Several primary cancers that are diagnosed or staged on CT wind up requiring bone scans for separate bone staging. For cancers of the lung and bronchus, it has been shown that twenty percent of bone involvement is underestimated, and bone scintigraphy is required to properly stage the bone. In the event of a missed bone metastasis in a patient with a primary lung cancer, the patient would unnecessarily undergo lung resection in an attempt to cure the disease, resulting in pain, morbidity and possibly mortality that would have been avoided had the patient been appropriately diagnosed already with metastatic disease. By detecting these lesions early on, patients can be appropriately upstaged and futile surgeries and radiation treatments can be avoided. If one could detect these early lesions at the time of initial diagnosis, which is generally done by CT scan, then one could avoid a bone scan altogether. Similarly, there are cases of indeterminate bone lesions in which there are some characteristics that suggest a benign diagnosis and some suggest a malignant diagnosis, which are seen on CT scans of the chest, abdomen and pelvis. In these situations, the ability to directly image the bone marrow elements will increase diagnostic confidence towards either a benign or a malignant diagnosis.

Accordingly, lesions that could ordinarily only be diagnosed using magnetic resonance imaging (MRI) can be diagnosed using CT scanning, which is invaluable for patients who cannot undergo MRI, for example, due to medical implants that react poorly with the high magnetic fields necessary for MRI. Further, CT scanning is quicker, and less expensive, and provides superior spatial resolution over MRI, as well as being less prone to motion artifact. It can also provide bone and soft tissue information in a single scan. Dual energy CT scanners have also demonstrated some increased sensitivity to bone marrow abnormalities. The vast majority of CT scanners in current use, however, utilize a single-energy profile. Further, the use of two x-ray tubes generally increases the radiation dose when compared with signal-to-noise matched single-energy acquisitions. It is thus believed that a single-energy image processing routine in accordance with an aspect of the present invention will be a useful alternative for detecting otherwise occult bone marrow lesions in CT.

Tissue suppression also has potential uses in other areas of the body, where interfaces between tissues result in diagnostic errors, such as brain imaging. Although occurring on a larger size scale than trabeculae and bone marrow, the gyri of the brain and the intervening fluid-filled sulci result in an analogous partial volume averaging problem. Particularly on the more superior axial images of the brain, partial volume averaging of normal brain cortex with adjacent cerebrospinal fluid can result in the appearance of low attenuation cortex, a sign of edema and suggestive of stroke. A radiologist may overcall stroke in this situation, or more commonly, under call the lesion because it is attributed to partial volume averaging, rather than true pathology. Suppressing the fluid in the sulci during image reconstruction using this tissue suppression algorithm can increase the conspicuity and detection rate of cortical brain infarctions.

FIG. 1 illustrates a first example of a single-energy computed tomography (CT) imaging system 10 in accordance with an aspect of the present invention. The illustrated implementation exploits the fact that normal tissues in the body, such as fat, soft tissue, fluid, bone, and air, are distinguishable by well-separated attenuation values and the high throughplane spatial resolution of modern CT scanners, which can be used to identify small tissue components within larger, clinically usable voxels. For example, a volume of tissue represented by a voxel having a thickness of three mm may contain bone, fat and fluid. If the voxel is interrogated as a whole, the resulting attenuation would be the average of all three of these tissue components.

Modern detectors can provide a z-axis resolution on the order of a one-quarter to one-half of a millimeter, such that the scanner can interrogate multiple parts within a voxel of three to five mm. The small slices are too small to be useful clinically, as the data set is too large for storage, the images are relatively noisy, and the sheer volume of images would take far too long to review. Therefore, radiologists still review images in larger slices, typically three to five millimeters. To generate these larger voxels, the higher resolution data set is typically reconstructed to average all data points in the z-axis to create a three millimeter voxel.

In accordance with an aspect of the invention, the system 10 includes a CT detector assembly 12 that scans a region of interest to provide axial attenuation values and a display 14 for showing reconstructed CT images to a user. The axial attenuation values from the detector assembly 12 are provided to an image processing element 20 to transform the axial attenuation values into images comprehensible to a human operator.

In one implementation, the axial attenuation data is provided to a reconstruction element 22 that generates a first set of cross-sectional CT images having a first axial resolution from the provided CT scan data. For example, the reconstruction element 22 can utilize a filtered back projection process to provide the first set of cross-sectional CT images. In one implementation, each of the first set of cross-sectional CT images can have an axial resolution on the order of a one-quarter to one-half of a millimeter. The first set of CT image slices is then provided to a tissue suppression component 24, configured to identify voxels within the first set of cross-sectional CT images representing tissues that it is desirable to suppress from their characteristic attenuation values. Specifically, a range of attenuation associated with the tissue to be suppressed can be defined, and all voxels within the defined range of attenuation values can be identified and flagged.

In another implementation, the tissue suppression component 24 acts directly on the axial attenuation data from the detector assembly 12, such that axial attenuation values within a defined range are suppressed before the axial attenuation values are provided to the reconstruction element 22. The reconstruction element 22 then provides the first set of CT image slices from the suppressed axial attenuation data.

An averaging component 26 generates a second set of cross-sectional CT images having an axial resolution less than that of the first set of cross-sectional CT images (e.g., having wider constituent voxels). In one implementation, each of the second set of cross-sectional CT images can have an axial resolution of three millimeters. For example, each of the second set of cross-sectional CT images can be generated as a voxel-by-voxel averaging of a subset of the first set of cross-sectional CT images. It will be appreciated that the subsets of the first set of cross-sectional CT images can be discrete or contain a small amount of overlap among subjects represent adjacent images of the second set of cross-sectional CT images. In accordance with an aspect of the present invention, the averaging component 26 does not utilize any of the pixels flagged at the filtering component in generating the second set of cross-sectional CT images, such that the final averaged voxels within the second set of cross-section CT images are generated from attenuation values from only the non-suppressed tissues. The second set of cross-sectional CT images can then be displayed to a clinician at the display 14 via a user interface 28.

Bone marrow is composed of varying quantities of fatty marrow, hematopoietic marrow, trabecular bone, and, in cases of pathology such as neoplasm, soft tissue. In a CT image, fatty marrow has a negative attenuation value, bone has attenuation values of at least one hundred Hounsfield Units (HU), and pathologic soft tissue processes have attenuation values of approximately forty to eighty HU. Hematopoietic marrow, which has some fat insinuated between cellular elements, has an attenuation value between that of fat and soft tissue. When a soft tissue process, such as a neoplasm, is present in an area that normally contains only fatty marrow (e.g., in the shaft of a long bone), the difference in attenuation between these tissues provides sufficient contrast to identify the pathologic lesion.

In areas of high trabecular bone content, such as a vertebral body or the pelvis, conventional volume averaging includes trabecular bone in the attenuation values of both pathologic and normal tissues. In these cases, the final voxel attenuation values are in the range expected for bone because of the higher attenuation of bone relative to either fat or soft tissue. The difference in attenuation between normal and abnormal tissues is also reduced because of the inclusion of trabecular bone in both regions. This leads to decreased conspicuity of soft tissue marrow-replacing lesions. Additionally, trabecular bone can be heterogeneously distributed within the same bone and between adjacent bones, resulting in a wide range of attenuation. This makes it difficult to determine whether visible differences in attenuation are the result of this heterogeneous distribution or due to underlying pathology.

Accordingly, in one implementation, the image processing element 20, and more specifically the tissue suppression component 24, can be configured to suppress the contribution of trabecular bone from image reconstruction. Specifically, tissue suppression component 24 can utilize a threshold attenuation of seventy HU, near the established upper range of known soft tissue attenuation values, can be used with the expectation that any tissue present with an attenuation exceeding this threshold would represent bone. By using a tissue suppression process in accordance with the present invention, the appearance of trabecular bone in CT images can be reduced and the appearance of the bone marrow can be made more homogeneous, allowing for visualization of bone marrow-replacing lesions that could not be seen with standard CT reconstruction, such as lesions in areas of high trabecular bone density in which there is minimal or no bone destruction.

Figures 2, 3:
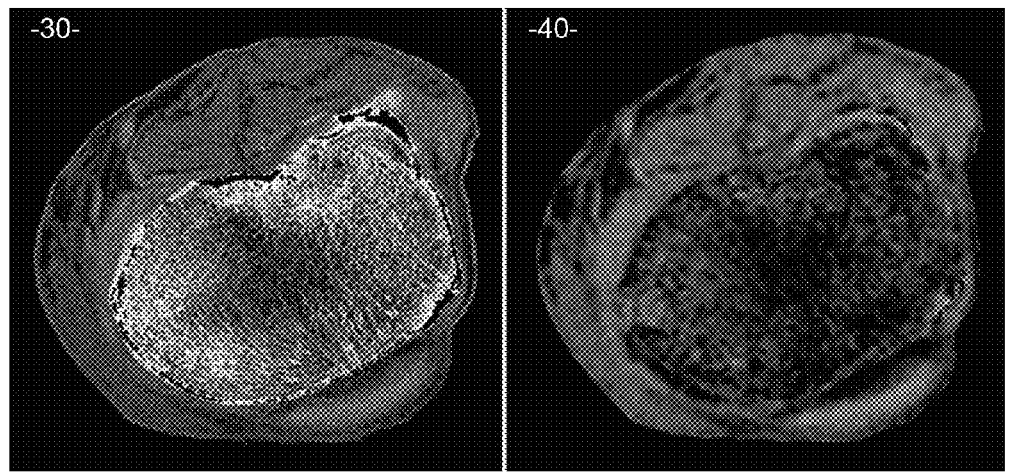
FIG. 2 illustrates a representative five millimeter axial CT image of the proximal tibia of a cadaver using a standard CT scan.
FIG. 3 illustrates a representative five millimeter axial CT image of the proximal tibia of a cadaver using the system of FIG. 1.

FIGS. 2 and 3 illustrate representative five millimeter axial CT images of the proximal tibia of a cadaver. The image 30 of FIG. 2 was created using a standard reconstruction. It will be noted that most of the intertrabecular marrow fat is obscured due to the volume averaging. The image 40 of FIG. 3 was generated using a tissue suppression function in accordance with an aspect of the present invention. The effects of the trabecular tissue suppression cause the marrow fat to be depicted more homogenously, with an appearance similar to subcutaneous fat within the same image. This ensures that any anomalies within the tissue will be more apparent.

Figure 4:
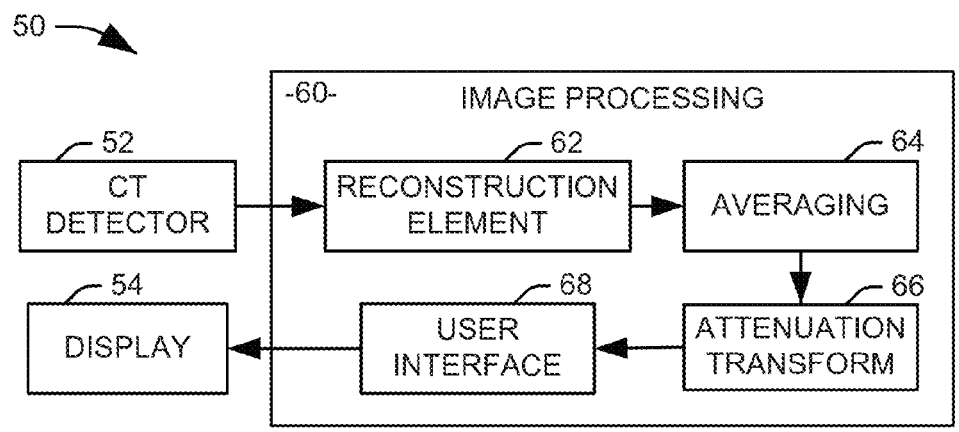
FIG. 4 illustrates a second example of a CT imaging system in accordance with an aspect of the present invention.

FIG. 4 illustrates a second example of a computed tomography (CT) imaging system 50 in accordance with an aspect of the present invention. Conventionally, CT displays a direct linear relationship between attenuation and brightness which makes sense from a physics perspective and is consistent with the historical development from radiographs. In accordance with an aspect of the present invention, however, the illustrated system 50 applies a transform to the CT data to disrupt this direct linear relationship between to better accentuate the differences between various tissue structures of interest.

For example, on a conventional CT image, a liver infarction results in the organ becoming darker while appendicitis results in the adjacent fat getting brighter. This is because the baseline attenuation values of the involved tissues lie either above or below the attenuation value of fluid so that when fluid enters the tissue, it will tend to change the attenuation of the tissue toward that of fluid. This makes for more complex image interpretation. The particular tissue of interest must be considered. For example, if the tissue is bone, then lowering of attenuation is of interest, if it the tissue is mesentery, then higher attenuation is of interest. MRI, with its ability to directly measure water content, displays abnormal tissues as bright, regardless of the tissue type. This is a current advantage over CT. The illustrated system adjusts CT to display the changes in these tissues to reflect the pathologic changes in an easily accessible manner.

To this end, the system 50 includes a CT detector assembly 52 that scans a region of interest to provide axial attenuation values and a display 54 for showing reconstructed CT images to a user. The axial attenuation values from the detector assembly 52 are provided to an image processing element 60 includes a reconstruction element 62 that generates a first set of cross-sectional CT images having a first axial resolution from the provided CT scan data. The first set of CT image slices is provided to an averaging component 64 that generates a second set of cross-sectional CT images having an axial resolution less than that of the first set of cross-sectional CT images. For example, each of the second set of cross-sectional CT images can be generated as a voxel-by-voxel averaging of a subset of the first set of cross-sectional CT images.

The second set of cross-sectional CT images is provided to an attenuation transform component 66 configured to apply a piecewise transform function to the attenuation values in the first set of cross-sectional CT images to provide a set of transformed cross-sectional CT images. Effectively, the attenuation transform component 66 maps the attenuation value associated with each voxel to an associated brightness value. The transformed CT images are then displayed at the display 54 via an associated user interface 68. It will be appreciated that, although the attenuation transform 66 is shown and described as acting on the second set of cross-sectional CT images, in one implementation the attenuation transform can be applied to the first set of cross-sectional CT images prior to the averaging at the averaging component.

Figure 5:
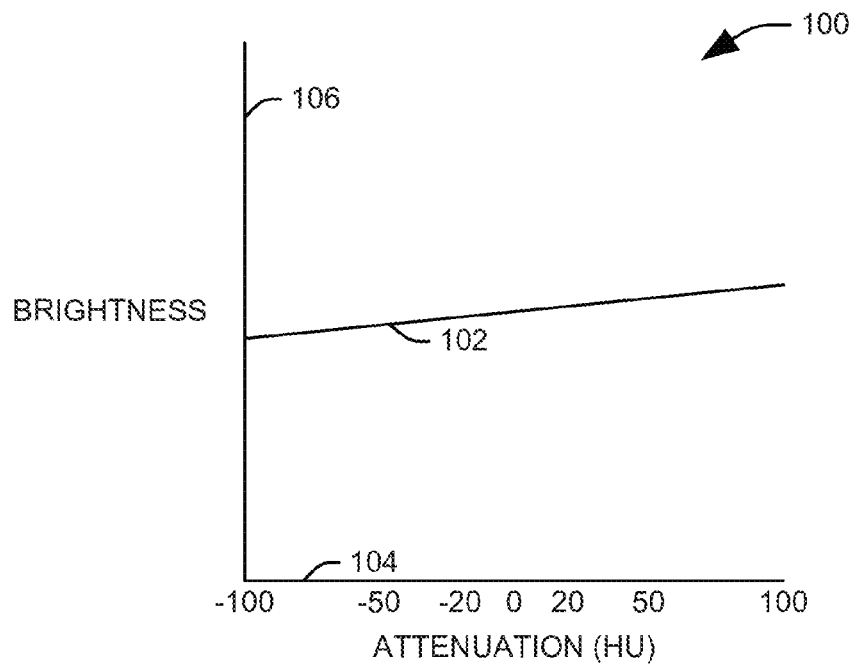
FIG. 5 is a graph illustrating a conventional mapping of attenuation values from a CT scan to brightness values.

In accordance with an aspect of the present invention, a proper subset of the available attenuation values are mapped across the available dynamic range of the display 54 associated with the user interface 68. For example, FIG. 5 is a graph 100 illustrating a conventional mapping 102 of attenuation values from a CT scan, which range from −1000 HU to 1000 HU, with only the range from −100 HU to 100 HU represented on the horizontal axis 104, to the available dynamic range of the brightness of the displayed image, represented by the vertical axis 106. It will be noted that the values between −100 HU and 100 HU take up only around ten percent of the available dynamic range.

Figure 6:
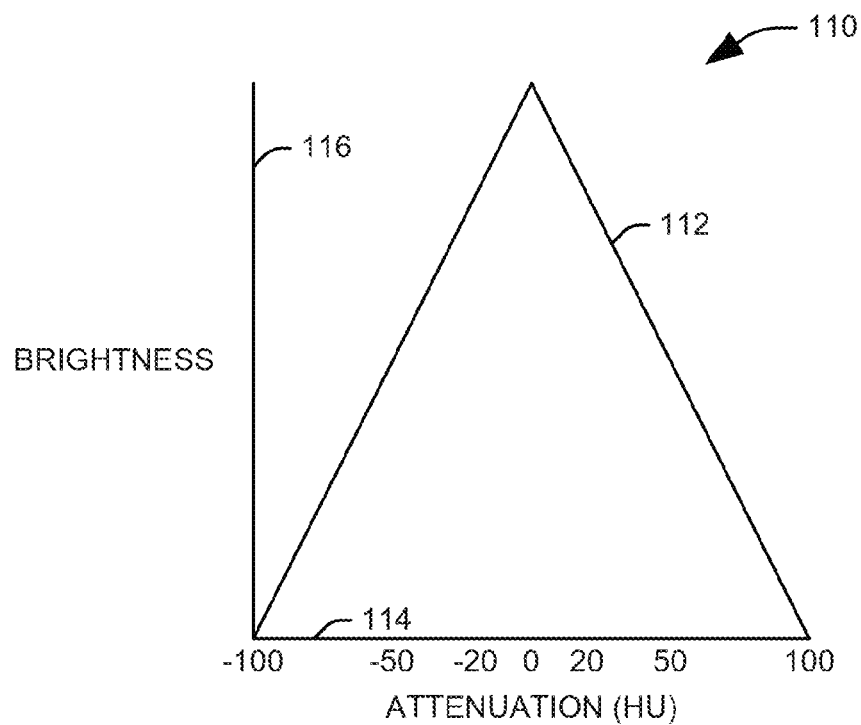
FIG. 6 is a first graph illustrating an example mapping of attenuation values from a CT scan to brightness values in accordance with an aspect of the present invention.

FIG. 6 is a first graph 110 illustrating an example mapping 112 of the attenuation values from a CT scan represented on the horizontal axis 114, to the available dynamic range of the brightness of the displayed image, represented by the vertical axis 116. In the illustrated mapping, it will be noted that all values less than −100 HU and greater than 100 HU are not represented. In practice, they will have a lowest brightness of the available dynamic range. By mapping the voxels within this range of attenuation values to the entire dynamic range, the contrast among these voxels is already improved by approximately an order of magnitude.

Further, in according with an aspect of the present invention, all voxels having a positive attenuation value can be assigned as same brightness value as their additive inverse. In other words, a brightness of the displayed voxel will increase linearly from a lowest brightness value to a highest brightness value as an attenuation value of the voxels progresses from −100 HU to 0 HU, and the brightness of the displayed voxel will decrease linearly from a highest brightness value to a lowest brightness value as an attenuation value of the voxels progresses from 0 HU to 100 HU. The illustrated attenuation transform 112 is designed to accentuate the appearance of fluid within soft tissue. It will be appreciated that, while specific ranges for tissue can vary, the attenuation values for fat can generally include a range of approximately −100 HU to −1 HU, the attenuation values for fluid can generally include a range of approximately 0 HU to 20 HU, and the attenuation values for soft tissue can generally include a range of approximately 21 HU to 100 HU. By setting the peak brightness to coincide with the range of attenuation values associated with fluid, the detection of fluid within fat or soft tissue is greatly simplified.

For example, normal fatty marrow has an attenuation value around −100 HU, and will be displayed as essentially black after the attenuation transform 112. Pure fluid will appear extremely bright and will be easy to detect. According, in the event of a bone marrow edema, any fluid that has leaked into the marrow will cause the region of the edema to be significantly brighter, with the degree of brightness dependent on the ratio of fluid to fat. This applies to other soft tissue injuries that may develop a degree of edema as well. For example, tendons generally have attenuation values between 80 HU and 100 HU. The inversion of positive values shifts all of the voxels representing tendons to a range between −80 HU and −100 HU, giving them a fairly low brightness. Accordingly, when edema is present, the combination of the tendon and the edema will be significantly brighter than a normal tendon, simplifying identification of a tendon injury. Effectively, the illustrated attenuation transform 112 can provide an image similar to that of a fat-suppressed $T_2$ MRI image or an MRI image taken using Short TI Inversion Recovery (STIR) without all of the inherent disadvantages of MRI.

Figure 7:
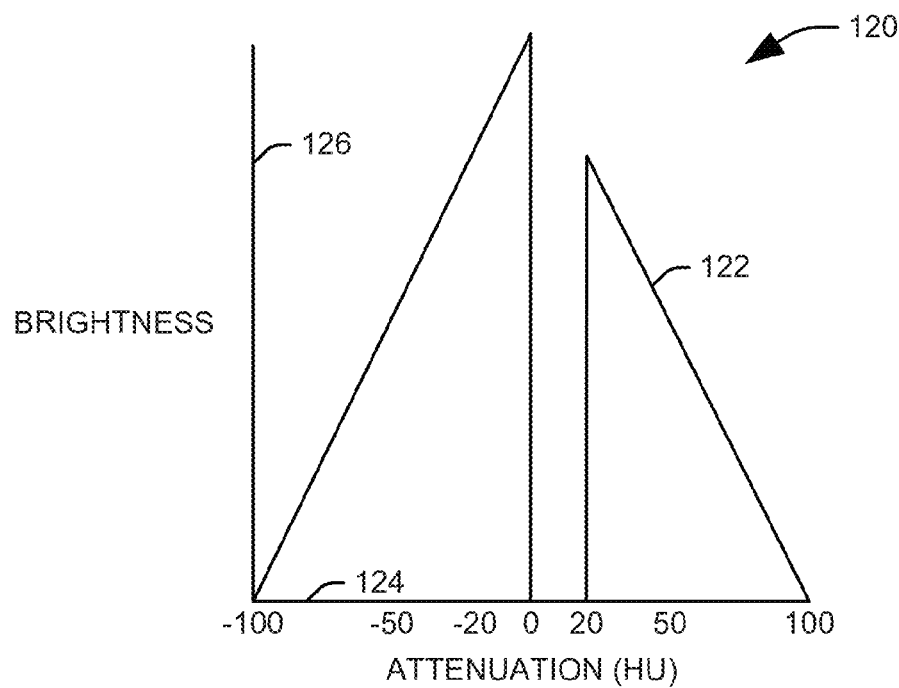
FIG. 7 is a second graph illustrating an example mapping of attenuation values from a CT scan to brightness values in accordance with an aspect of the present invention.

FIG. 7 is a second graph 120 illustrating an example mapping 122 of the attenuation values from a CT scan represented on the horizontal axis 124, to the available dynamic range of the brightness of the displayed image, represented by the vertical axis 126. In the illustrated transform, not only are voxels having a positive attenuation value assigned as same brightness value as their additive inverse, but the fluid range, between 0 HU and 20 HU, are suppressed and displayed as black. The illustrated attenuation transform 122 can provide an image similar to that of an MRI image taken using Fluid Attenuated Inversion Recovery (FLAIR) without the disadvantages inherent to MRI.

Figure 8:
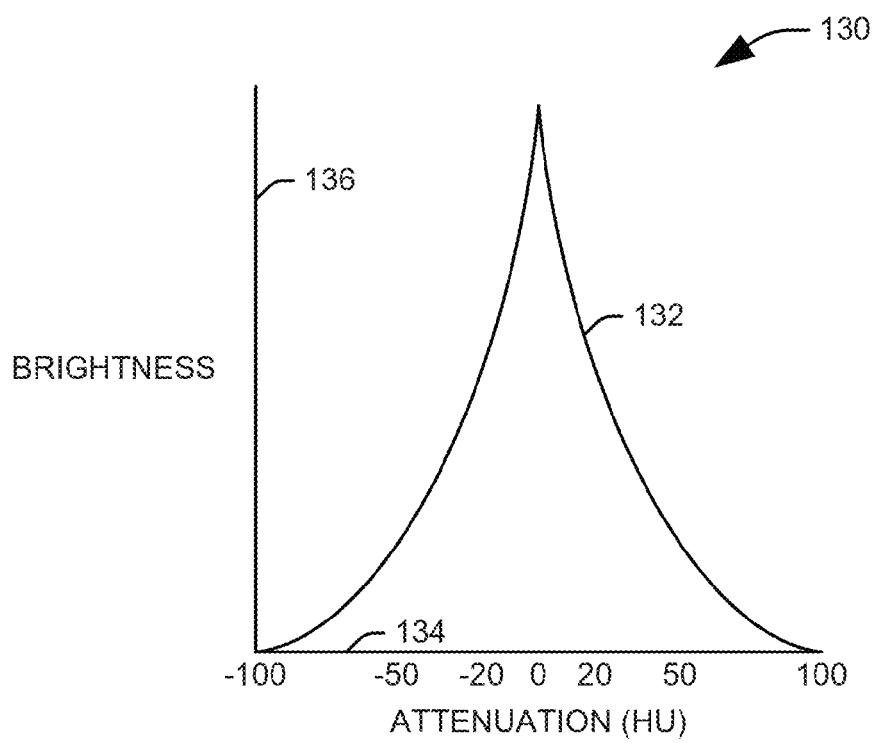
FIG. 8 is a third graph illustrating an example mapping of attenuation values from a CT scan to brightness values in accordance with an aspect of the present invention.

FIG. 8 is a third graph 130 illustrating an example mapping 132 of the attenuation values from a CT scan represented on the horizontal axis 134, to the available dynamic range of the brightness of the displayed image, represented by the vertical axis 136. In the illustrated transform 132, not only are all voxels having a positive attenuation value assigned as same brightness value as their additive inverse, but the relationship between the attenuation values and the brightness values is exponential instead of linear. In other words, a brightness of the displayed voxel will increase exponentially from a lowest brightness value to a highest brightness value as an attenuation value of the voxels progresses from −100 HU to 0 HU, and the brightness of the displayed voxel will decrease exponentially from a highest brightness value to a lowest brightness value as an attenuation value of the voxels progresses from 0 HU to 100 HU. This exponential mapping allows small variations in the attenuation values of voxels to cause noticeable changes in the brightness of the displayed voxels. In the illustrated example, the mapped brightness values are selected to be most sensitive to variation of the attenuation values near 0 HU. This could be useful, for example, in determining if edema is present in soft tissue having attenuation values near the lower end of the normal range (e.g., around 20 HU).

Figure 9:
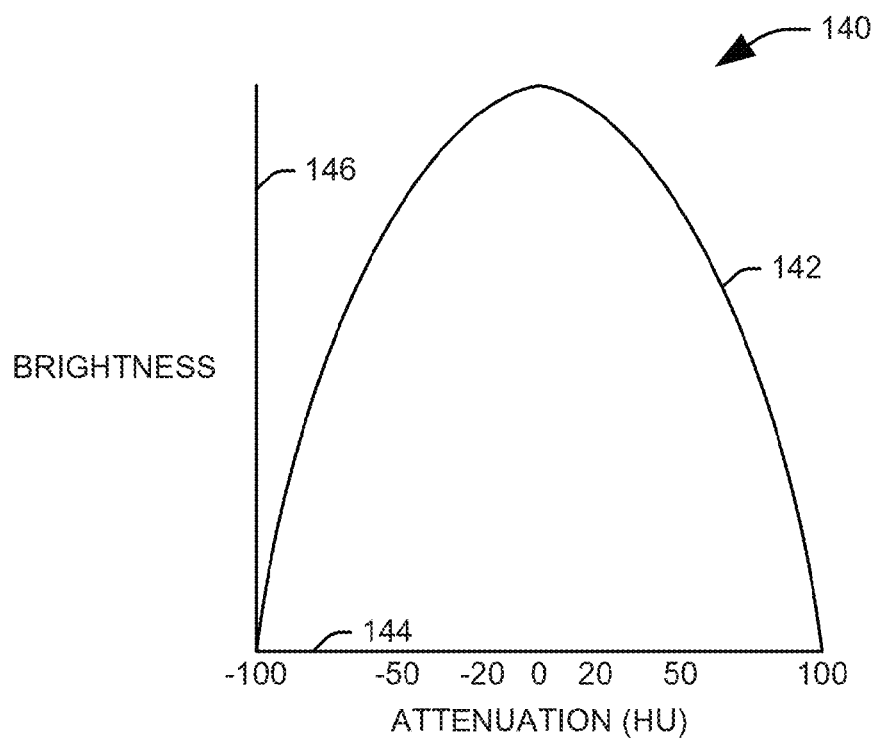
FIG. 9 is a fourth graph illustrating an example mapping of attenuation values from a CT scan to brightness values in accordance with an aspect of the present invention.

FIG. 9 is a fourth graph 140 illustrating an example mapping 142 of the attenuation values from a CT scan represented on the horizontal axis 144, to the available dynamic range of the brightness of the displayed image, represented by the vertical axis 146. Like the transform of FIG. 8, all voxels having a positive attenuation value assigned as same brightness value as their additive inverse, and the assigned brightness values vary exponentially with the attenuation values. In the illustrated example, the mapped brightness values are selected to be most sensitive to variation of the attenuation values near the endpoints of the range of interest, specifically near −100 HU and 100 HU. For example, fat-containing bone marrow would normally have an attenuation value of −100 HU, but with a small amount of edema, this value can increase minimally to −95 HU. Even with the enhanced visibility provided by the transforms of FIGS. 6 and 7, this variation might not be noticeable in the displayed image. By utilizing the exponential relationship between attenuation and brightness, the brightness of the edematous fat will be increased noticeably despite the relatively small difference in the attenuation value.

Figure 10:
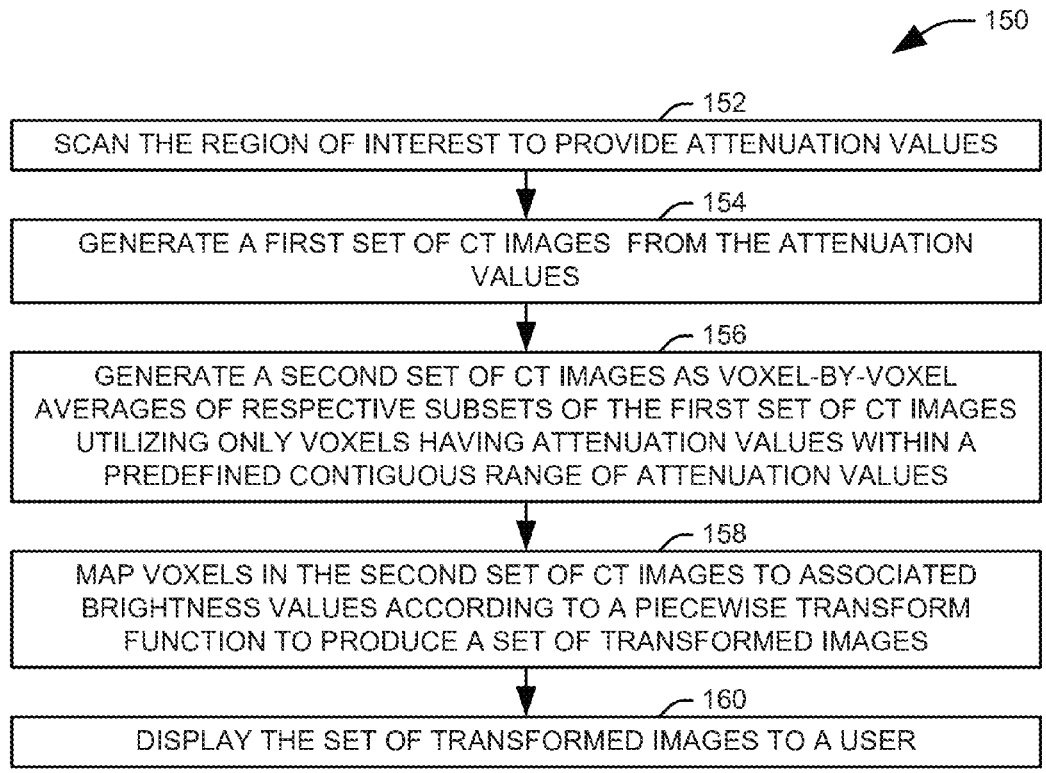
FIG. 10 illustrates a method for providing CT scan data for a region of interest in accordance with an aspect of the present invention.

In view of the foregoing structural and functional features described above, a method in accordance with various aspects of the present invention will be better appreciated with reference to FIG. 10. While, for purposes of simplicity of explanation, the method of FIG. 10 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 10 illustrates a method 150 for CT scanning. At 152, a region of interest is scanned to provide a set of axial attenuation values. At 154, a first set of cross-sectional CT images, having a first axial resolution, are generated from the provided axial attenuation values. For example, the first set of cross-sectional CT images can be formed via filtered back projection. At 156, a second set of cross-sectional CT images, having a second axial resolution less than that of the first axial resolution, is generated as a voxel-by-voxel averaging of respective subsets of the first set of cross-sectional CT images. The voxel-by-voxel averaging only utilizes voxels having attenuation values within a predefined contiguous range of attenuation values. Accordingly, the influence of voxels outside of a range of interest on the average can be eliminated, allowing for better resolution in regions of closely mixed tissues.

At 158, voxels in the second set of cross-sectional CT images are mapped to associated brightness values according to a piecewise transform function to produce a set of transformed images. In one implementation, the piecewise transform function includes a first region in which all of the attenuation values are mapped to a lowest brightness value, a second region in which the brightness increases linearly with the attenuation value from a lowest brightness value to a peak brightness value, a third region in which the brightness decreases linearly with the attenuation value from the brightness value to the lowest brightness value, and remains at the lowest brightness value in a fourth region. In another implementation, the piecewise transform function includes a first region in which all of the attenuation values are mapped to a lowest brightness value, a second region in which the brightness increases exponentially with the attenuation value from a lowest brightness value to a peak brightness value, a third region in which the brightness decreases exponentially with the attenuation value from the brightness value to the lowest brightness value, and remains at the lowest brightness value in a fourth region. The set of transformed images are displayed to the user at 160.

Figure 11:
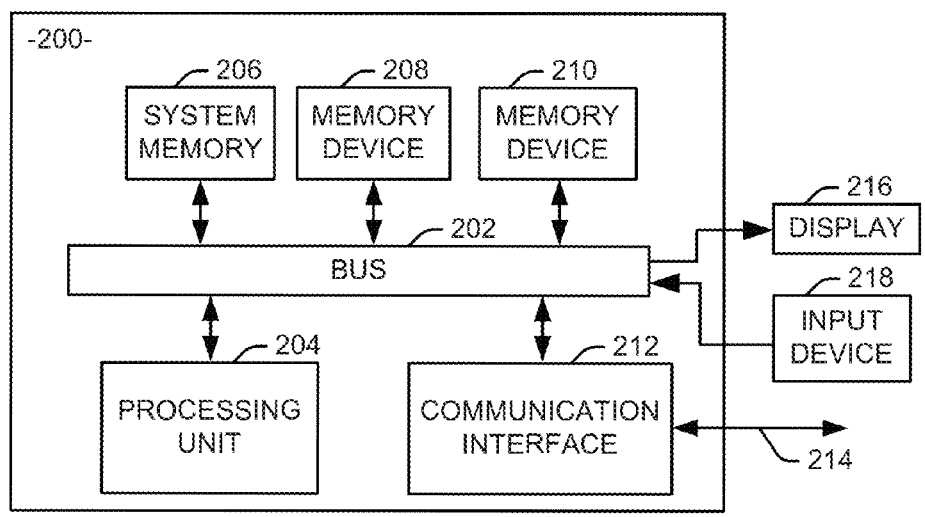
FIG. 11 is a schematic block diagram illustrating an exemplary system of hardware components capable of implementing examples of the systems and methods disclosed herein.

FIG. 11 is a schematic block diagram illustrating an exemplary system 200 of hardware components capable of implementing examples of the systems and methods disclosed in FIGS. 1-10, such as the imaging systems illustrated in FIGS. 1 and 4. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a CT imaging system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

From the above description of the invention, those skilled in the art will perceive improvements, changes, and modifications. Such improvements, changes, and modifications within the skill of the art are intended to be covered by the appended claims.

Having described the invention, I claim:

1. A non-transitory computer readable medium storing executable instructions comprising:
   a reconstruction element configured to generate a first set of cross-sectional computed tomography (CT) images from data provided from the CT scan;
   a tissue suppression component configured to identify values of pixels within the first set of cross-sectional CT images, representing tissues that it is desirable to suppress according to their characteristic attenuation values;
   an averaging component configured to generate a second set of cross-sectional CT images, having an associated axial resolution less than an axial resolution of the first set of cross-sectional CT images, a voxel-by-voxel averaging of a subset of the first set of cross-sectional CT images, the voxel-by-voxel averaging omitting any voxels in the subset of the first set of cross-sectional CT images that is identified at the tissue suppression component; and
   a user interface configured to provide the set of cross-sectional CT images to a user at an associated display.

2. The non-transitory computer readable medium of claim 1, the tissue suppression component being configured to identify all voxels within a defined range of attenuation values.

3. The non-transitory computer readable medium of claim 2, wherein the defined range of attenuation values is all attenuation values greater than seventy Hounsfield Units.

4. The non-transitory computer readable medium of claim 1, further comprising an attenuation transform component configured to map voxels in the second set of cross-sectional CT images to associated brightness values according to a piecewise transform function to produce a set of transformed images, the user interface providing a set of transformed images to the display.

5. A non-transitory computer readable medium storing executable instructions comprising:
  an attenuation transform component configured to map voxels in a received set of cross-sectional computed tomography (CT) images to associated brightness values according to a piecewise transform function to produce a set of transformed images, the piecewise transform function assigning all voxels having an attenuation value either below a first attenuation value or above a second attenuation value to a lowest brightness value, such that an entire dynamic range of the brightness values is assigned to voxels having attenuation values between the first attenuation value and the second attenuation value and a highest brightness value is assigned to a third attenuation value, with the piecewise transform function comprising a first linear mapping of attenuation values between the first attenuation value and the third attenuation value across the entire dynamic range of the brightness values such that the brightness value increases linearly with the attenuation value and a second linear mapping of attenuation values between the third attenuation value and the second attenuation value across the entire dynamic range of the brightness values such that the brightness value decreases linearly with the attenuation value; and
  a user interface configured to provide the set of transformed images to a user at an associated display.

6. The non-transitory computer readable medium of claim 5, further comprising:
  a reconstruction element configured to generate the received set of cross-sectional CT images as a first set of cross-sectional CT images, having a first axial resolution, from the provided CT scan data; and
  an averaging component configured to generate a second set of cross-sectional CT images, having an axial resolution less than that of the first set of cross-sectional CT images, from the set of transformed images, the user interface being configured to provide the second set of cross-sectional CT images.

7. The non-transitory computer readable medium of claim 6, further comprising a tissue suppression component configured to identify voxels within the first set of cross-sectional CT images representing tissues that it is desirable to suppress according to their characteristic attenuation values, and the averaging component being configured to generate the second set of cross-sectional CT images without utilizing the voxels identified by the tissue suppression component.

8. The non-transitory computer readable medium of claim 5, further comprising:
  a reconstruction element configured to generate a first set of cross-sectional CT images, having a first axial resolution, from the provided CT scan data; and
  an averaging component configured to generate a second set of cross-sectional CT images, having an axial resolution less than that of the first set of cross-sectional CT images, from the first set of cross-sectional CT images, attenuation transform receiving the second set of cross-sectional CT images as the set of received images.

9. The non-transitory computer readable medium of claim 5, wherein the first attenuation value is equal to −100 HU, the second attenuation value is equal to 100 HU, and the third attenuation value is equal to 0 HU.

10. A method for providing computed tomography (CT) scan data for a region of interest comprising:
  scanning the region of interest to provide a set of axial attenuation values;
  generating a first set of cross-sectional CT images, having a first axial resolution, from the provided axial attenuation values;
  generating a second set of cross-sectional CT images, having a second axial resolution less than that of the first axial resolution, as a voxel-by-voxel averaging of respective subsets of the first set of cross-sectional CT images, wherein the voxel-by-voxel averaging only utilizes voxels having attenuation values within a predefined contiguous range of attenuation values;
  mapping voxels in the second set of cross-sectional CT images to associated brightness values according to a piecewise transform function to produce a set of transformed images, the mapping comprising:
    assigning all voxels having an attenuation value either below a first attenuation value or above a second attenuation value to a lowest brightness value, such that an entire dynamic range of the brightness values is assigned to voxels having attenuation values between the first attenuation value and the second attenuation value;
    assigning a highest brightness to a third attenuation value;
    mapping attenuation values between the first attenuation value and the third attenuation value across the entire dynamic range of the brightness values such that the brightness value increases exponentially with the attenuation value; and
    mapping attenuation values between the third attenuation value and the second attenuation value across the entire dynamic range of the brightness values such that the brightness value decreases exponentially with the attenuation value; and
  displaying the set of transformed images to a user.

11. A non-transitory computer readable medium storing executable instructions comprising:
  an attenuation transform component configured to map voxels in a received set of cross-sectional computed tomography (CT) images to associated brightness values according to a piecewise transform function to produce a set of transformed images, the piecewise transform function assigning all voxels having an attenuation value either below a first attenuation value or above a second attenuation value to a lowest brightness value, such that an entire dynamic range of the brightness values is assigned to voxels having attenuation values between the first attenuation value and the second attenuation value and comprising a first mapping of attenuation values between the first attenuation value and a third attenuation value across the entire dynamic range of the brightness values such that the brightness value increases linearly with the attenuation value, a second mapping of attenuation values between the third attenuation value and a fourth attenuation value to the lowest brightness value, and a third mapping of attenuation values between the fourth attenuation value and the third attenuation value such that the brightness value decreases linearly from a first brightness value less than the highest brightness value to a lowest brightness; and
a user interface configured to provide the set of transformed images to a user at an associated display.

* * * * *